United States Patent [19]

Rauckhorst, III

[11] Patent Number: 5,569,850

[45] Date of Patent: Oct. 29, 1996

[54] ICE DETECTOR

[75] Inventor: Richard L. Rauckhorst, III, North Canton, Ohio

[73] Assignee: The B.F. Goodrich Company, Akron, Ohio

[21] Appl. No.: 437,004

[22] Filed: May 8, 1995

[51] Int. Cl.⁶ ...................................................... G02N 1/00
[52] U.S. Cl. ........................ 73/170.26; 340/580; 29/610.1
[58] Field of Search ........................ 73/170.26; 29/610.1; 244/134 R, 134 A, 134 D, 134 F; 340/580, 581; 374/112, 109; 324/694

[56] References Cited

U.S. PATENT DOCUMENTS

| | | | |
|---|---|---|---|
| 3,178,560 | 4/1965 | Mapp et al. | 244/134 D |
| 4,732,351 | 3/1988 | Bird | 244/134 D |
| 4,745,803 | 5/1988 | Haavasoia | 73/170.26 |
| 4,765,187 | 8/1988 | Weinstein | 73/304 |
| 4,766,369 | 8/1988 | Weinstein | 340/580 X |
| 4,897,597 | 1/1990 | Whitener | 73/170.26 X |
| 4,914,416 | 4/1990 | Kunikane | 29/610.1 X |
| 4,942,078 | 7/1990 | Newman et al. | 244/134 R X |
| 4,996,493 | 2/1991 | Monat et al. | 340/580 X |
| 5,134,380 | 7/1992 | Jonas | 340/580 X |
| 5,191,791 | 3/1993 | Gerardi et al. | 73/178 |
| 5,394,340 | 2/1995 | Inkpen et al. | 340/580 X |
| 5,398,547 | 3/1995 | Gerardi et al. | 73/170.26 |

OTHER PUBLICATIONS

G. A. Hickman & J. J. Gerardi of Innovative Dynamics for Lewis Research Center, "Autonomous Deicing System for Airplane Wing", NASA Tech Briefs, Oct. 1993, p. 30.

*Primary Examiner*—Richard Chilcot
*Assistant Examiner*—Elizabeth L. Dougherty
*Attorney, Agent, or Firm*—Richard A. Romanchik

[57] ABSTRACT

An ice detector 110 includes a pair of electrodes 122, 124 connected by a pair of leads 116, 118 to a control unit 120 which measures the impedance (or other parameters) between leads 116 and 118 to thereby sense and detect ice or other contaminants formed on top thereof. Electrodes 122, 124 are integrated into patch 134 and comprised of a top layer 142 of conductive resin, a middle layer 144 of conductive cloth and a bottom layer 146 of conductive resin.

25 Claims, 2 Drawing Sheets

ICE DETECTOR

TECHNICAL FIELD

The present invention relates to ice detectors, and more particularly, to a total impedance type ice detector patch for aircraft surfaces.

BACKGROUND OF THE INVENTION

Under certain operating conditions, aircraft are vulnerable to the accumulation of contaminants on external component surfaces or skins. Examples of such contaminants include ice, water, and mixtures thereof. If left unchecked, the accumulation of ice can eventually so laden the aircraft with additional weight and so alter airfoil configuration as to cause undesirable flying conditions. The ability to detect the accumulation of ice on such surfaces, and the ability to measure the accumulated thickness thereof so as to identify dangerous flight conditions, has therefore become highly desirable.

A number of different kinds of contaminant detectors have been utilized for such objectives. Among them are capacitive ice detectors, examples of which can be found in U.S. Pat. Nos. 4,766,369 to Weinstein and 5,398,547 to Gerardi et al., both of which are hereby incorporated herein by reference.

The Weinstein invention is comprised of metal electrodes mounted near the outer surface of an aircraft. A small section of the outer surface is removed and replaced by embedding material which is preferably either plastic or an epoxy type material. The ice detector is embedded in the embedding material slightly below the outer surface. The electrodes do not touch each other and hence the presence of a material such as ice in the vicinity of the electrodes causes a change in the capacitance between the electrodes.

The Gerardi et al. patent discloses an ice sensor integrated in a pneumatic deicing boot. A short range sensor has positive electrode wires and ground wires separated by an electrical insulator, preferably neoprene. A long range sensor is fabricated from a series of positive electrode wires formed above guard electrode wires which are disposed above ground electrode wires. Two insulating sheets separate the three sets of wires. The wires and insulating sheets are configured and then potted in an elastic dielectric compound similar to RTV silicon. Gerardi et al. also states that conductive elastic fabric can replace the wires.

Efforts to improve such ice detection systems have led to continuing developments to improve their cost, manufacturability, reliability, usefulness, and efficiency.

DISCLOSURE OF THE INVENTION

An object of the present invention is to provide an ice detector integrated into a resilient patch attachable to an airfoil or other surface.

According to the present invention, a method of making an ice detector includes the steps of:

a) disposing a conductive cloth between conductive resin layers;

b) curing said conductive cloth and said conductive resin layers together to form an electrode assembly; and, c) integrating said electrode assembly into a resilient patch.

According to another aspect of the present invention, an ice detector includes:

an electrode assembly comprised of a conductive cloth cured between conductive resin layers, said electrode assembly being integrated into a resilient patch.

The present invention provides a highly sensitive ice detector which is easy to manufacture, is highly reliable, is low cost, and is retrofittable onto existing aircraft.

These and other objects, features and advantages of the present invention will become more apparent in the light of the detailed description of exemplary embodiments thereof, as illustrated by the drawings.

BEST MODE FOR CARRYING OUT THE INVENTION

Figure 1:
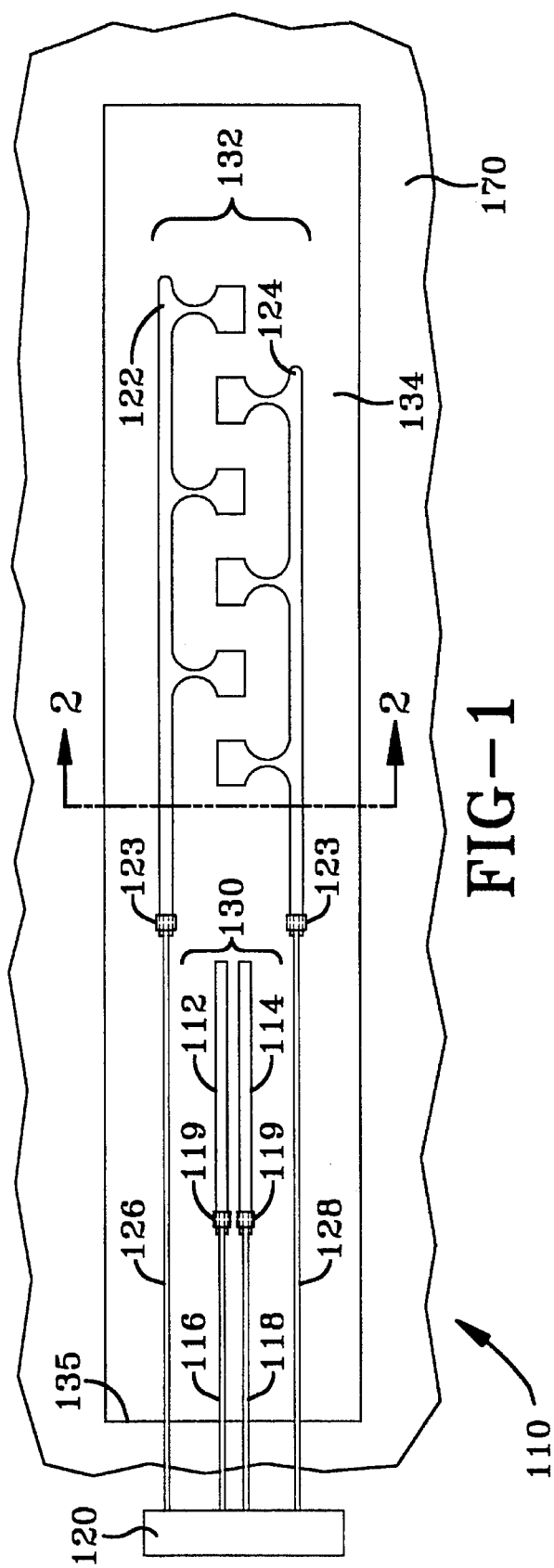
FIG. 1 is a top view of an ice detector in accordance with a first embodiment of the present invention.

Referring now to FIG. 1, an ice detector 110 in accordance with the present invention includes a first pair of electrodes (or elements) 112, 114 connected by a pair of leads 116, 118 to a controller means or control unit 120. Electrodes 112, 114 comprise a first type (Type 1) of ice detector or sensor 130. Another pair of electrodes 122, 124 are connected to control unit 120 via leads 126, 128 and comprise a second type (Type 2) of ice detector or sensor 132. Control unit 120 measures the impedance between leads 116 and 118. Control unit 120 may also measure other parameters (such as capacitance) required to sense and detect ice or other contaminants formed on top of detector 110. Sensors 130, 132 are integrated into a resilient (or elastomeric) ice detection patch 134 described in greater detail hereinafter. Patch 134 may be attached or bonded to an airfoil 170 or other substrate. It is to be noted that other electrode configurations not explicitly shown herein may be utilized in the present invention.

Figure 2:
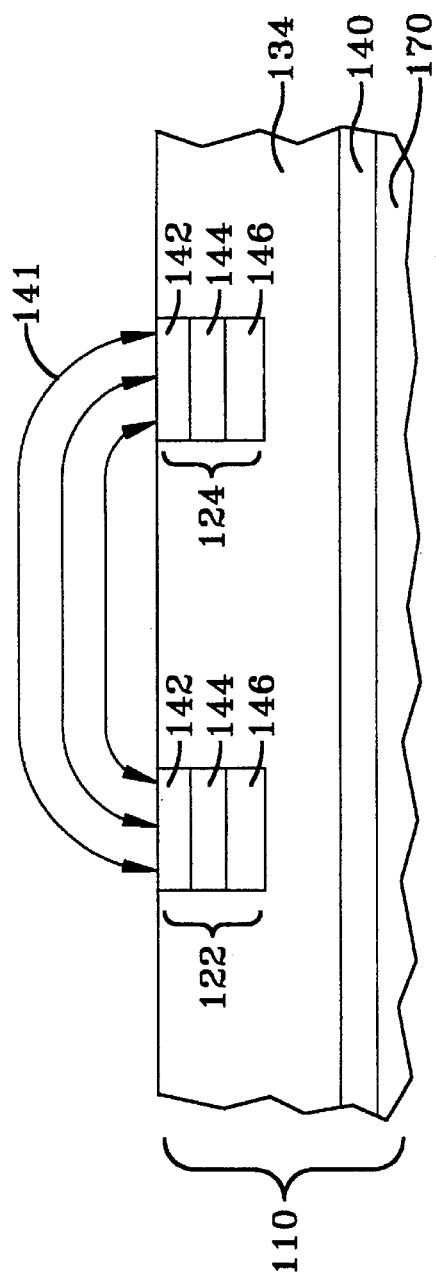
FIG. 2 is a cross sectional view of an ice detector in accordance with the present invention, taken along line 2—2 of FIG. 1.

Referring now to FIG. 2, an ice detector 110 in accordance with the present invention includes a non-conductive patch 134 disposed over a guard layer 140. Guard layer 140 is utilized to minimize stray capacitance by eliminating electric field lines between the electrodes and the airfoil surface 170. An electric field, as indicated by lines 141, between electrodes 122 and 124 will be affected by the accretion of ice or other contaminant 138 in proximity with the electrodes. Electrodes 122, 124 are integrated into patch 134 and are comprised of a top layer 142 of conductive resin, a middle layer 144 of conductive cloth and a bottom layer 146 of conductive resin. Electrodes 122, 124 are used to measure ice 138 or other contaminants disposed on the exposed side 139 of detector 110. Patch 134 is preferably an approximately 0.02 inch thick non-conductive urethane film, such as catalog number 121JC202 available from the B. F. Goodrich Company. Guard layer 140 is preferably an approximately 0.003 inch thick conductive elastomer, such as catalog number 0121JC205 available from the B. F. Goodrich Company. Top electrode layer 142 is preferably an approximately 0.003 inch thick layer of conductive urethane resin, such as catalog number 0121JC205 available from the B. F. Goodrich Company. Middle electrode layer 144 is preferably an approximately 0.003 inch thick layer of conductive cloth. The preferred cloth is comprised of matrix aluminum (Al), fiberglass woven, corona treated and primed with a phenolic adhesive, such as catalog number EC3901 available from the 3M Corporation. Conductive cloth 144 may also be a knit nylon fabric, such as Code 925 available from the Fairlane Company. Bottom electrode layer 146 is preferably an approximately 0.004 inch thick layer of conductive urethane resin, such as catalog number 0121JC205 available from the B. F. Goodrich Company.

Fabrication of ice detector 110 is as follows. A tool with an approximately 0.010 inch cavity provided therein having a width at least as wide as the maximum width of the electrode. The conductive urethane resin of top electrode layer 142 is thereafter disposed in the cavity. Then the middle electrode conductive cloth layer 144 is placed onto the urethane resin. Then the bottom electrode urethane layer 146 is cast on top of the conductive cloth layer. The three layers are then removed from the tool and cured at 280 degrees F. at 35 psi for 40 minutes. After curing, the three layers are cut into the shape of the electrode. For instance, the three layers may be cut into the shape of electrodes 122, 124. A connector, 119, 123 such as a 0.001 inch thick piece of copper foil is wrapped around the electrode at the location of connection to the lead wire (e.g. wires 116, 118, 126, 128). The lead wire is then soldered to the copper foil. A layer of non-conductive urethane resin, which will make up part of the patch 134 has the electrode pattern cut out of it. The electrode is then disposed in the matching pattern of the patch 134 (thereby making up a patch subassembly). An additional layer of non-conductive neoprene, such as catalog number 65227 available from the B. F. Goodrich Company is then disposed on the bottom or unexposed side of the patch subassembly to thereby make an ice detector assembly 110. The entire ice detector assembly is then placed on a build metal, bagged, and cured at 280 degrees F., at 35 psi for 45 minutes. If necessary, the guard layer 140 is bonded to the bottom or unexposed side of ice detector 110 after curing.

Ice detector 110 may then be combined further into a deicer assembly, or it can be utilized as an ice detecting "patch kit" which can be applied almost anywhere on the aircraft. If the ice detector 110 is utilized as a patch kit, the preferred thickness of the non-conductive patch is preferably 0.015 inches thick. An appropriate bonding glue, such as catalog number 1300L manufactured by the 3M corporation or a H-Kit available from the B. F. Goodrich Company, is necessary to bond the patch kit to the aircraft.

Figure 3:
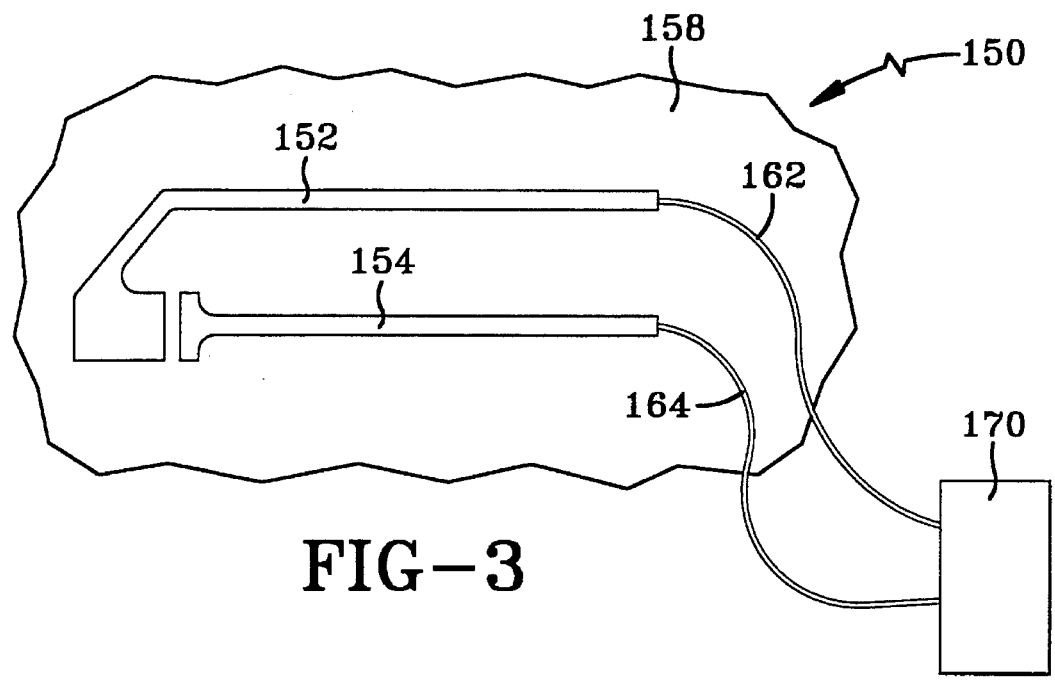
FIG. 3 is a top view of an ice detector in accordance with an additional embodiment of the present invention.

Referring now to FIG. 3, an ice detector 150 in accordance with another embodiment of the present invention includes electrodes 152, 154, integrated into a non-conductive patch 158. Electrodes 152, 154 are connected via leads 162, 164 to a control unit 170. Electrodes 152, 154 make up a third type (Type 3) of ice detector or sensor.

Figure 4:
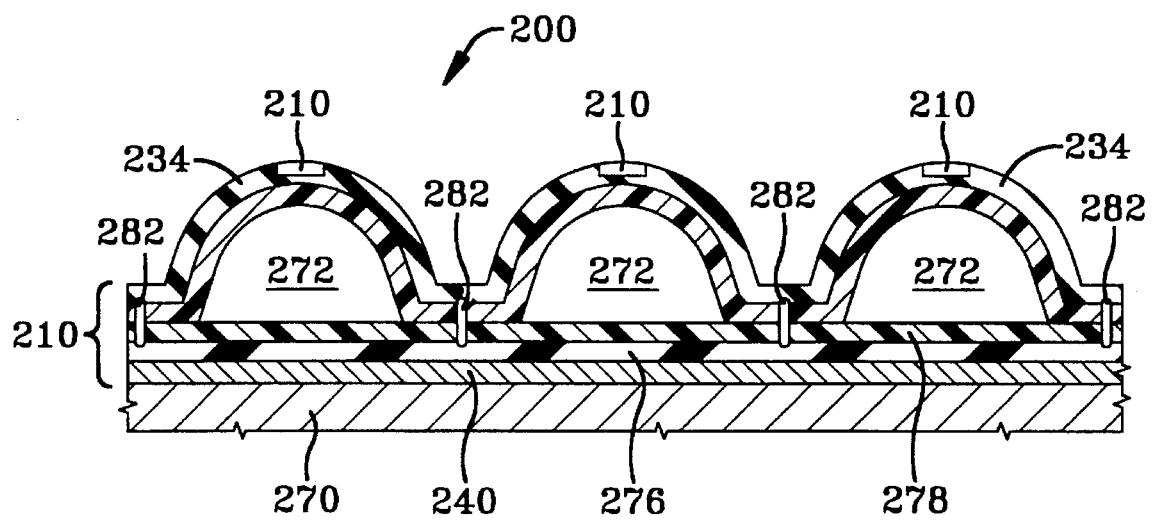
FIG. 4 is a cross sectional view of an ice detector in accordance with the present invention that is integrated into a pneumatic deicer.

Referring now to FIG. 4, a pneumatic deicing system 200 in accordance with the present invention which includes a deicer assembly 210 comprised substantially of a composite of flexible materials. The deicer assembly 210 is formed as part and parcel of an airfoil skin 270 thereby defining the outer contour of the airfoil. Deicing system 210 is typically disposed on the leading edge of the airfoil and is thereby referred to as a leading edge deicer. The preferred method of integrating the deicer assembly 210 with the airfoil 270 is to provide an the airfoil, manufacture the deicer assembly as a separate entity, and bond or attach the deicer assembly onto the airfoil at the desired location. The preferred bonding means to attach a deicer assembly 210 to the airfoil 270 is to apply an adhesive, such as catalog number 1300L manufactured by the 3M corporation, to both contacting surfaces.

The principle inflatable portion of the deicer assembly 210 is a plurality of tube-like passages 272 formed therein and arranged substantially parallel to one another. Tube-like passages expand or inflate when provided a pressurized fluid, such as air. All inflatable tube-like passages 272 are fluidly connected at one end of deicer assembly 210. The preferred construction for deicer assembly 210 is a composite, comprised from bottom (the side of material bonded to the airfoil) to top of: a) a guard layer 240 such as guard layer 140 described hereinbefore; b) a bottom layer or ply 276 of flexible material, such as neoprene; c) a first intermediate, nonstretchable layer or ply 278 of nonstretchable fabric such as nonstretchable nylon which is rubber coated on one side; c) a second intermediate, layer or ply 280 of stretchable fabric, such as stretchable nylon which is rubber coated one side; and, e) a top layer or ply 234 of a tough yet pliable weather impervious material, such as non-conductive urethane or neoprene. An inflation pattern is created by sewing the nylon layers 278, 280 together in a predetermined pattern using thread 282. The preferred material for thread 282 is nylon or KEVLAR. KEVLAR is a registered trademark of E. I. Dupont Denemours Corporation. Layers 234–280 and 276–278 may be bonded together utilizing an appropriate cement, such as catalog number CHEMLOC 220 manufactured by the Lord Corporation. CHEMLOC is a registered trademark of the Lord Corporation. The inflation pattern consists of a series of high inflation areas or passageways 272, created by stitches 282. Ice detectors similar to ice detectors 110 described hereinbefore are integrated into top layer 234. Of course, deicing patch 110 could be utilized with and integrated into other types of deicing systems or other systems.

It is to be noted that controllers 120, 170 may be any of a number of controllers which measure impedance or capacitance known to those skilled in the art, such as those described in the heretofore mentioned U.S. Pat. Nos. 4,766,369 to Weinstein and 5,398,547 to Gerardi et al., hereby incorporated herein by reference.

Although the invention has been shown and described with exemplary embodiments thereof, it should be understood by those skilled in the art that the foregoing and various other changes, omissions and additions may be made therein and thereto without departing from the spirit and the scope of the invention.

I claim:

1. A method of making an ice detector comprising the steps of:

a) disposing a conductive cloth between conductive resin layers;

b) curing said conductive cloth and said conductive resin layers together to form an electrode assembly; and, c) integrating said electrode assembly into a resilient patch.

2. A method of making an ice detector according to claim 1, wherein said step c of claim 1, comprises the steps of:

cutting said electrode assembly into a predetermined electrode shape;

cutting said predetermined electrode shape in said resilient patch; and, placing said electrode assembly in said resilient patch leaving at least a portion of said electrode exposed; and, curing said electrode assembly and said resilient patch together.

3. A method of making an ice detector according to claim 1, further comprising the step of attaching said resilient patch to an airfoil surface.

4. A method of making an ice detector according to claim 1, further comprising the step of integrating said resilient patch into a leading edge deicing assembly.

5. A method of making an ice detector according to claim 1, wherein said conductive resin comprises urethane resin.

6. A method of making an ice detector according to claim 1, wherein said conductive cloth comprises aluminum.

7. A method of making an ice detector according to claim 1, wherein said conductive cloth comprises corona treated aluminum primed with an adhesive.

8. A method of making an ice detector according to claim 1, wherein said conductive cloth comprises knit nylon.

9. A method of making an ice detector according to claim 1, wherein said patch comprises urethane.

10. A method of making an ice detector according to claim 1, wherein said patch comprises neoprene.

11. A method of making an ice detector according to claim 1, further comprising the step of integrating said resilient patch into a pneumatic deicing assembly.

12. A method of making an ice detector according to claim 1, further comprising the steps of wrapping metal foil around said electrode assembly and electrically connecting a wire to said metal foil.

13. A method of making an ice detector according to claim 1, further comprising the step of connecting said electrode assembly to a controller means.

14. An ice detector comprising;
an electrode assembly comprised of a conductive cloth cured between conductive resin layers, said electrode assembly being integrated into a resilient patch.

15. An ice detector according to claim 14, wherein said resilient patch is attached to an airfoil surface.

16. An ice detector according to claim 14, wherein said resilient patch is integrated into a leading edge deicing assembly.

17. An ice detector according to claim 14, wherein said conductive resin comprises urethane resin.

18. An ice detector according to claim 14, wherein said conductive cloth comprises aluminum.

19. An ice detector according to claim 14, wherein said conductive cloth comprises corona treated aluminum primed with an adhesive.

20. An ice detector according to claim 14, wherein said conductive cloth comprises knit nylon.

21. An ice detector according to claim 14, wherein said patch comprises urethane.

22. An ice detector according to claim 14, wherein said patch comprises neoprene.

23. An ice detector according to claim 14, wherein said resilient patch is integrated into a pneumatic deicing assembly.

24. An ice detector according to claim 14, further comprising metal foil wrapped around said electrode assembly and wire electrically connected to said metal foil.

25. An ice detector according to claim 14, further comprising controller means connected to said electrode assembly.

* * * * *